(12) United States Patent
Huang et al.

(10) Patent No.: US 8,269,049 B2
(45) Date of Patent: Sep. 18, 2012

(54) METHOD OF PRODUCING DIETHYLENE-GLYCOL TERT-BUTYL ETHER USING ISOBUTYLENE AND DIETHYLENE GLYCOL

(75) Inventors: Ming-Yu Huang, Taipei (TW); Jen-Chun Chang, Taipei (TW); Jann-Chen Lin, Taipei (TW); Kuen-Hai Lin, Taipei (TW); Jung-Chung Wu, Taipei (TW)

(73) Assignee: Chinese Petroleum Corp., Taipei (TW)

( * ) Notice: Subject to any disclaimer, the term of this patent is extended or adjusted under 35 U.S.C. 154(b) by 393 days.

(21) Appl. No.: 12/651,166

(22) Filed: Dec. 31, 2009

(65) Prior Publication Data

US 2011/0160492 A1    Jun. 30, 2011

(51) Int. Cl.
    *C07C 41/42*    (2006.01)

(52) U.S. Cl. .................................... 568/679; 568/699
(58) Field of Classification Search .............. None
    See application file for complete search history.

(56) References Cited

U.S. PATENT DOCUMENTS

| | | | | |
|---|---|---|---|---|
| 1,968,033 | A * | 7/1934 | Evans et al. | 568/678 |
| 4,299,997 | A * | 11/1981 | Matsumoto et al. | 568/678 |
| 4,368,337 | A * | 1/1983 | Tawara et al. | 568/613 |
| 5,552,024 | A * | 9/1996 | Chang et al. | 203/64 |
| 6,264,800 | B1 * | 7/2001 | Gupta | 203/96 |

* cited by examiner

*Primary Examiner* — Rosalynd Keys
(74) *Attorney, Agent, or Firm* — Jackson IPG LLC

(57) ABSTRACT

The present invention fabricates diethylene-glycol tert-butyl ether (DEGtBE) by using isobutylene and diethylene glycol (DEG) coordinated with an acidic cation exchanged resin as catalyst. Through two stages of vacuum distillations, highly selective and pure DEGtBE is produced. Moreover, a byproduct of diethylene-glycol di-tert-butyl ether (DEGDtBE) can be recycled.

20 Claims, 13 Drawing Sheets

| reaction conditions | | | IB⁼ conversion rate (%) | Product selectivity (%) | | |
|---|---|---|---|---|---|---|
| temperature (°C) | DEG/IB⁼ mole ratio | [H⁺]/IB⁼ mole ratio | | DEGtBE | DEGDtBE | Octene |
| 50 | 2.0 | 0.05 | 91.7 | 91.0 | 5.4 | 3.6 |
| 60 | 2.0 | 0.05 | 94.9 | 88.4 | 8.2 | 3.5 |
| 70 | 2.0 | 0.05 | 91.2 | 85.4 | 11.3 | 3.4 |
| 80 | 2.0 | 0.05 | 90.2 | 84.2 | 13.0 | 2.8 |
| 90 | 2.0 | 0.05 | 85.4 | 85.2 | 11.2 | 3.5 |
| 100 | 2.0 | 0.05 | 82.8 | 85.2 | 12.0 | 2.8 |
| 110 | 2.0 | 0.05 | 78.5 | 85.6 | 11.2 | 3.1 |

FIG.2a

| reaction conditions | | | $IB^=$ conversion rate (%) | product selectivity (%) | | |
|---|---|---|---|---|---|---|
| temperature (°C) | $DEG/IB^=$ mole ratio | $[H^+]/IB^=$ mole ratio | | DEGtBE | DEGDtBE | Octene |
| 60 | 2.0 | 0.03 | 86.9 | 87.8 | 9.3 | 2.9 |
| 60 | 2.0 | 0.05 | 94.9 | 88.4 | 8.2 | 3.5 |
| 60 | 2.0 | 0.07 | 96.5 | 87.5 | 8.5 | 4.0 |

FIG.2b

| reaction conditions | | | IB= conversion rate (%) | product selectivity (%) | | |
|---|---|---|---|---|---|---|
| temperature (°C) | DEG/IB= mole ratio | [H+]/IB= mole ratio | | DEGtBE | DEGDtBE | Octene |
| 60 | 1.5 | 0.05 | 88.5 | 83.6 | 11.7 | 4.7 |
| 60 | 2.0 | 0.05 | 94.9 | 88.4 | 8.2 | 3.5 |
| 60 | 3.0 | 0.05 | 91.2 | 92.3 | 4.6 | 3.1 |
| 60 | 3.5 | 0.05 | 88.4 | 92.3 | 3.1 | 4.5 |

FIG.2c

| reaction conditions | | | $IB^=$ conversion rate (%) | product selectivity (%) | | |
|---|---|---|---|---|---|---|
| temperature (°C) | DEG/$IB^=$ mole ratio | WHSV ($h^{-1}$) | | DEGtBE | DEGDtBE | Octene |
| 45 | 2.0 | 1.20 | 79.5 | 92.5 | 5.4 | 2.1 |
| 55 | 2.0 | 1.20 | 92.7 | 86.4 | 11.2 | 2.4 |
| 60 | 2.0 | 1.20 | 89.8 | 79.7 | 17.5 | 2.8 |
| 70 | 2.0 | 1.20 | 89.9 | 76.5 | 20.3 | 3.2 |
| 80 | 2.0 | 1.20 | 90.0 | 74.0 | 22.5 | 3.4 |

FIG.3a

| reaction conditions | | | IB⁼ conversion rate (%) | product selectivity (%) | | |
|---|---|---|---|---|---|---|
| temperature (°C) | DEG/IB⁼ mole ratio | WHSV (h⁻¹) | | DEGtBE | DEGDtBE | Octene |
| 55 | 1.5 | 1.20 | 89.5 | 82.2 | 15.1 | 2.6 |
| 55 | 2.0 | 1.20 | 92.7 | 86.4 | 11.2 | 2.4 |
| 55 | 3.0 | 1.20 | 88.6 | 90.4 | 7.4 | 2.2 |
| 55 | 4.0 | 1.20 | 84.5 | 93.5 | 5.0 | 1.5 |

FIG.3b

| reaction conditions | | | $IB^=$ conversion rate (%) | product selectivity (%) | | |
|---|---|---|---|---|---|---|
| temperature (°C) | $DEG/IB^=$ mole ratio | WHSV ($h^{-1}$) | | DEGtBE | DEGDtBE | Octene |
| 55 | 2.0 | 0.60 | 88.6 | 81.7 | 15.8 | 2.5 |
| 55 | 2.0 | 1.20 | 92.7 | 86.4 | 11.2 | 2.4 |
| 55 | 2.0 | 1.80 | 93.8 | 88.1 | 10.4 | 1.5 |
| 55 | 2.0 | 2.40 | 79.7 | 90.6 | 8.0 | 1.4 |
| 60 | 2.0 | 0.60 | 87.9 | 75.8 | 23.2 | 1.0 |
| 60 | 2.0 | 1.20 | 89.8 | 79.7 | 17.5 | 2.8 |
| 60 | 2.0 | 1.80 | 94.2 | 81.3 | 17.0 | 1.7 |

FIG.3c

|  | 1st time | 2nd time | 3rd time | 4th time | 5th time |
|---|---|---|---|---|---|
| first stage 90°C 150 Torr | distillate product/water 1/1 (w/w) distilled DEGDtBE (%) | 95.5 | 96.0 | 95.4 | 96.1 | 96.3 |
|  | DEGDtBE in residual liquor (%) | 6.47 | 4.23 | 3.67 | 1.25 | 0.53 |
| second stage 100°C 1 Torr | residual liquor after first stage distilled DEGDtBE (%) | 99.9 | --- | --- | --- | --- |
|  | DEGDtBE in residual liquor (%) | 0 | --- | --- | --- | --- |

FIG.4

| temperature (°C) | 50 | 60 | 75 | 90 |
|---|---|---|---|---|
| DEGDtBE conv. % | 38.3 | 58.0 | 80.5 | 86.5 |
| DEGtBE/DEGDtBE (mole/mole) | 1.990 | 1.869 | 1.788 | 1.742 |

FIG.5

| temperature (°C) | 50 | 60 | 75 | 90 |
|---|---|---|---|---|
| DEGDtBE conv. % | 1.0 | 13.1 | 23.2 | 25.8 |
| select. % DEGtBE | 100 | 100 | 100 | 100 |
| select. % DEG | 0 | 0 | 0 | 0 |

FIG.6

METHOD OF PRODUCING DIETHYLENE-GLYCOL TERT-BUTYL ETHER USING ISOBUTYLENE AND DIETHYLENE GLYCOL

FIELD OF THE INVENTION

The present invention relates to fabricating diethylene-glycol tert-butyl ether (DEGtBE); more particularly, relates to using isobutylene (IB=) and diethylene glycol (DEG) coordinated with a solid acid catalyst for fabricating DEGtBE having high selectivity and purity through two stages of vacuum distillations under certain conditions.

DESCRIPTION OF THE RELATED ARTS

Because use of aromatic solvent is restricted owing to its high photochemical reactivity, other solvents like paraffin, cycloalkane and oxygen-containing solvent are used in replacement nowadays for not having photochemical reactivity. A widely used oxygen-containing solvent is a glycol ether compound having two functional groups with strong solvency: one is an ether group and the other is a hydroxyl group. The ether group is lipophilic. The hydroxyl group is hydrophilic. Hence, the glycol ether compound becomes a general solvent. For example, ethylene glycol (EG) methyl ether is a good surface coating solvent and an anti-icing agent for air-fuel. EG ethyl ether is used as an industrial solvent for paint, dye, resin, leather, etc.; or, a detergent for metal and glass. EG butyl ether is widely used in water borne coating for its good dispersion property. Furthermore, EG ether can be used in cosmetic, perfume, medicine, etc. Propylene glycol (PG) ether is used as solvent for alkyd resin and epoxy resin; and can be used in ink to make it water-soluble.

For now, usage amount of the EG ether is the greatest; then is the PG ether, including methyl, ethyl, propyl and butyl ether. Although EG ether is cheap, it is not environment protected and may do harm to human body. Yet, EG ether can be replaced with PG ether or DEG ether, where DEG ether is the development focus for the future.

General ether compounds are obtained through three methods. The first method is a traditional method using an epoxide and an ether, as shown in FIG. 7. This method is the main commercial method for producing various glycol ethers. However, raw materials used in this method are expensive in general; and many byproducts may be generated as well. Take EG products as examples. EG butyl ether may occupy about 85%; DEG butyl ether may occupy about 10%; and other multi-EG butyl ether may occupy about 5%. In the other hand, it is not easy to improve the production of DEG butyl ether through this method, for the other multi-EG butyl ether increases too on increasing selectivity of the DEG butyl ether.

The second method is to process an etherification with glycol and olefin, as shown in FIG. 8. The benefit of this method is that, after fractionation, a byproduct of double ether is recycled to a reactor for transetherification (as claimed in the U.S. Pat. No. 4,345,102) with heightened solving amount of IB=, enhanced reaction activity and restrained dibutyl ether (as claimed in the U.S. Pat. No. 4,299,997). However, this method requires highly active olefin and such an olefin generates byproducts of polymers easily, so only few glycol ethers are fabricated, where a main product is a butyl ether alcohol obtained with IB=. In addition, the product of ether alcohol and the byproduct of double ether may have an azeotrope and are thus hard to be separated.

The third method processes a dehydration synthesis with glycol and tert-butyl alcohol compound, as shown in FIG. 9. This method is operated with a strong acid catalyst ($H_2SO_4$) under a temperature between 140 and 180 Celsius degrees (° C.). However, this method is seldom used owing to the exacting reaction criteria and high corrosion of the strong acid catalyst under the high temperature. Hence, the prior arts do not fulfill all users requests on actual use.

SUMMARY OF THE INVENTION

The main purpose of the present invention is to use IB= and DEG coordinated with a solid acid catalyst for fabricating DEGtBE having high selectivity and purity through two stages of vacuum distillations under certain conditions.

The second purpose of the present invention is to recycle a byproduct of DEGDtBE for reaction while heightening solving amount of IB=, processing transetherification with DEG and restraining the byproduct from generating.

To achieve the above purposes, the present invention is a method of fabricating DEGtBE using IB= and DEG, comprising steps of: (a) obtaining DEG and IB= to be mixed in a reactor together with a catalyst of an acidic cation exchanged resin to obtain a glycol ether mixture, where the reactor has a reaction temperature between 30 and 150° C. and a reaction pressure between 15 and 500 pounds per square inch (psi); the catalyst has a mole ratio of acidity to IB= ($[H^+]/IB^=$) between 0.01 and 1.00; and the DEG has a mole ratio to IB= ($DEG/IB^=$) between 0.5 and 10.0; (b) processing the glycol ether mixture through a first stage of vacuum distillation then a second stage of vacuum distillation, where the first stage is a low vacuum water extraction distillation for separating octane and a byproduct of diethylene-glycol di-tert-butyl ether (DEGDtBE); and the second stage is a high vacuum distillation for separating un-reacted DEG and a product of DEGtBE; and (c) recycling the byproduct of DEGDtBE separated in the first stage into the reactor to process a transetherification with the DEG. Accordingly, a novel method of fabricating DEGtBE using IB= and DEG is obtained.

BRIEF DESCRIPTIONS OF THE DRAWINGS

The present invention will be better understood from the following detailed descriptions of the preferred embodiments according to the present invention, taken in conjunction with the accompanying drawings, in which FIG. 1 is the flow view according to the present invention;

FIG. 2a is the view showing the results of reaction activity and selectivity of the first preferred embodiment under different temperatures;

FIG. 2b is the view showing the results of reaction activity and selectivity of the first preferred embodiment under different catalyst acidities;

FIG. 2c is the view showing the results of reaction activity and selectivity of the first preferred embodiment under different DEG/IB= ratios;

FIG. 3a is the view showing the results of reaction activity and selectivity of the second preferred embodiment under different temperatures;

FIG. 3b is the view showing the results of reaction activity and selectivity of the second preferred embodiment under different DEG/IB= ratios;

FIG. 3c is the view showing the results of reaction activity and selectivity of the second preferred embodiment under different WHSVs;

FIG. 4 is the view shown the separation and purification;

FIG. 5 is the view showing the transetherification of DEGDtBE under different temperatures;

FIG. 6 is the view showing the cracking reactions of DEGDtBE under different temperatures.

DESCRIPTION OF THE PREFERRED EMBODIMENTS

The following descriptions of the preferred embodiments are provided to understand the features and the structures of the present invention.

Figure 1:
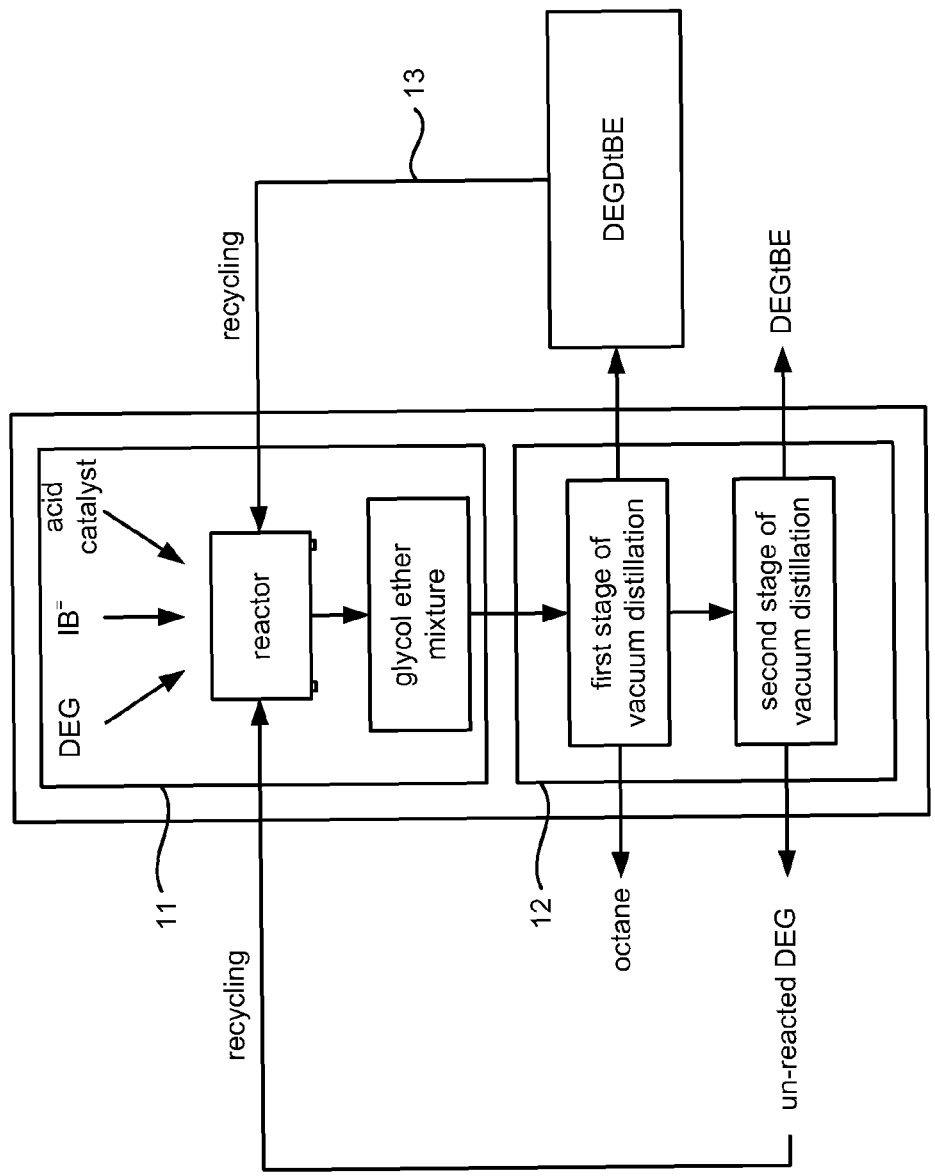
Figure 7:
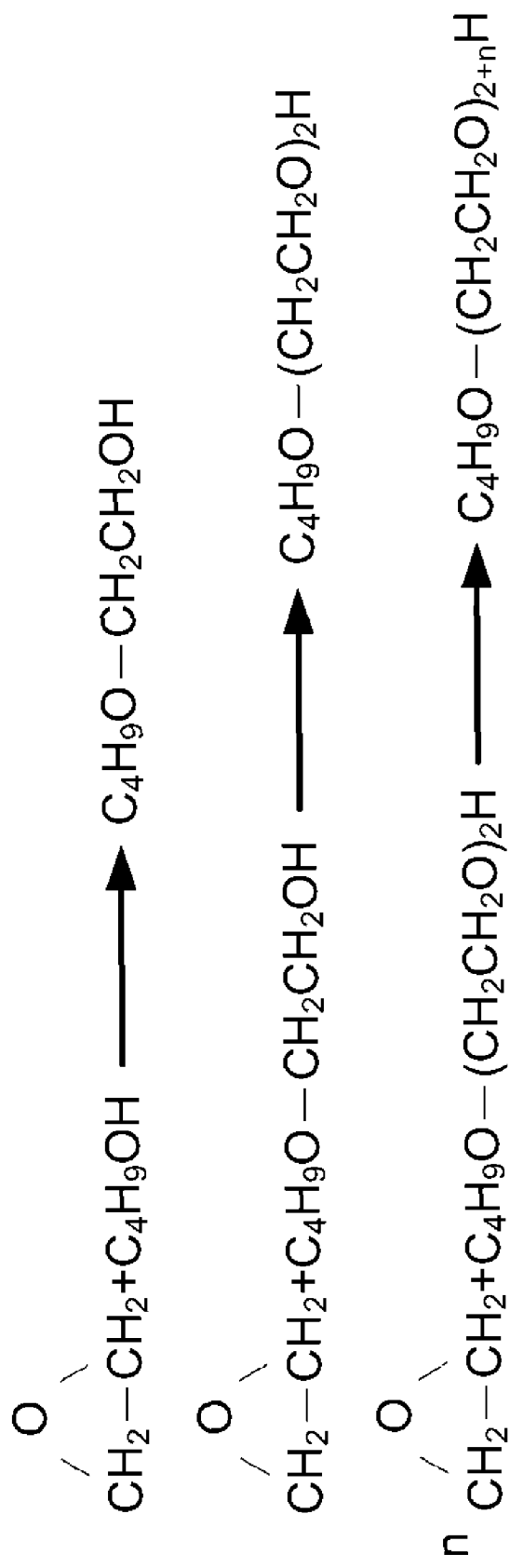
FIG. 7 to FIG. 9 are the views of the prior arts.
Figure 8:
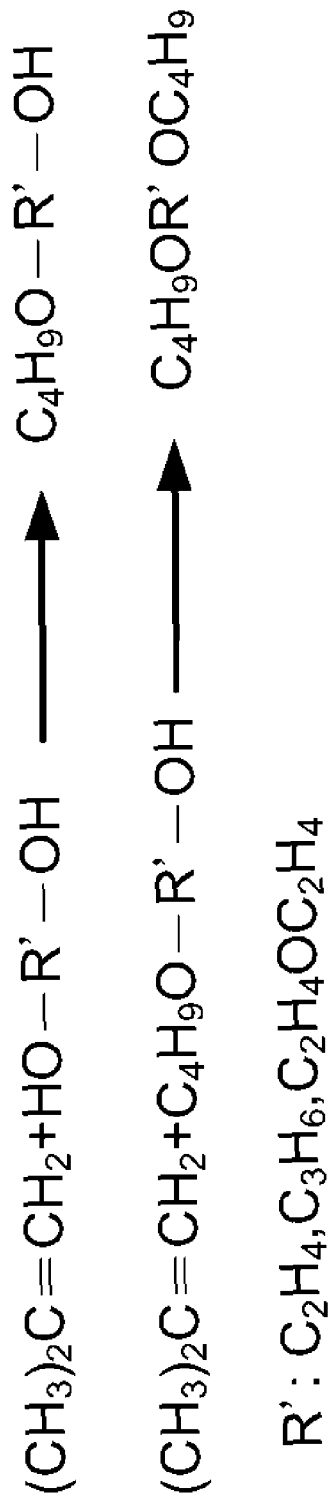
Figure 9:
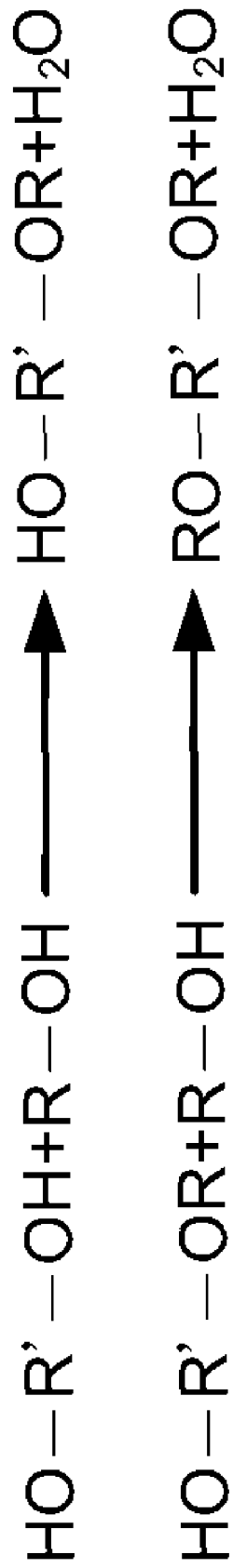

Please refer to FIG. 1, which is a flow view according to the present invention. As shown in the figure, the present invention is a method of fabricating diethylene-glycol tert-butyl ether (DEGtBE) using isobutylene ($IB^=$) and diethylene glycol (DEG), comprising the following steps:

(a) Obtaining glycol ether mixture 11: DEG and $IB^=$ are put into a reactor to be mixed together with a catalyst of an acidic cation exchanged resin for obtaining a glycol ether mixture, where the reactor has a reaction temperature between 30 and 150 Celsius degrees (° C.) and a reaction pressure between 15 and 500 pounds per square inch (psi); the catalyst has a mole ratio of acidity to $IB^=$ ($[H^+]/IB^=$) between 0.01 and 1.00; and the DEG has a mole ratio to $IB^=$ ($DEG/IB^=$) between 0.5 and 10.0.

(b) Processing two stages of vacuum distillations 12: The glycol ether mixture is processed through two stages of vacuum distillations. The first stage is a low vacuum water extraction distillation for separating octane and a byproduct of diethylene-glycol di-tert-butyl ether (DEGDtBE), where the first stage has a pressure between 50 and 500 torr and a temperature between 50 and 150° C.; and water added in the first stage has a weight ratio to the glycol ether mixture between 0.1 and 5.0. The second stage is a high vacuum distillation for separating un-reacted DEG and a product of DEGtBE, where the second stage has a pressure between 0.1 and 10 torr and a temperature between 50 and 150° C.

(c) Recycling byproduct 13: The byproduct of DEGDtBE separated in the first stage is recycled into the reactor for processing a transetherification with DEG, where the DEGDtBE has a weight ratio to the DEG between 0.002 and 1.0.

A device can be used in step (a) to process a continuous fixed-bed reaction with DEG, $IB^=$ and the catalyst under a temperature between 30 and 150° C., a pressure between 15 and 500 psi, a mole ratio of DEG to $IB^=$ between 0.5 and 10.0 and a weight hourly space velocity (WHSV) between 0.1 and 10.0 per hour ($h^{-1}$).

Accordingly, the present invention uses a cheap byproduct of DEG from ethylene glycol to be reacted with $IB^=$ contained in butane/butene raffinate. Then, with a solid acid catalyst, a product of DEGtBE with high selectivity and purity is fabricated under certain circumstances through two stages of vacuum distillations. Moreover, a byproduct of DEGDtBE is recycled for reaction while solving amount of $IB^=$ is heightened, transetherification is processed with DEG and the byproduct is restrained from generating.

A state of use according to the present invention comprises the following steps:

(a1) DEG, $IB^=$ and an acidic cation exchanged resin are put in a reactor for obtaining a glycol ether mixture under a temperature between 50 and 60° C. and pressure between 50 and 200 psi, where an acidity of the resin to $IB^=$ lies between 0.04 and 0.06; DEG has a mole ratio to $IB^=$ between 2.0 and 3.0; $IB^=$ is contained in a C4 mixture, like a butene mixture, to be inlet with a content ratio between 10 and 100 weight percent (wt %); and the resin is a cation exchanged resin processed through an acidification for obtaining a sulfo group ($-SO_3H$).

(b1) The glycol ether mixture obtained in step (a1) is processed through two stages of vacuum distillations for separation and purification. The first stage is a low vacuum water extraction distillation for separating octane and a byproduct of DEGDtBE, which has a pressure controlled between 100 and 200 torr and a temperature controlled between 65 and 105° C. The second stage is a high vacuum distillation for separating un-reacted DEG and a product of DEGtBE, which has a pressure controlled between 0.3 and 1.0 torr and a temperature controlled between 80 and 110° C. Therein, water added in step (a1) has a weight ratio to the glycol ether mixture between 0.25 and 1.0.

The byproduct of DEGDtBE separated in step (b1) is recycled to the reactor for a transetherification with DEG, where DEGDtBE has a weight ratio to DEG between 0.01 and 0.1; the DEGDtBE recycled to the reactor contains DEG; and the DEG had a content ratio between 1 and 100 wt %.

A device can be used in step (a1) to process a continuous fixed-bed reaction with DEG, $IB^=$ and the resin under a temperature between 45 and 55° C., a pressure between 50 and 200 psi, a mole ratio of DEG to $IB^=$ between 1.5 and 2.5 and a WHSV between 1.2 and 2.0 $h^{-1}$.

Please refer to FIG. 2a to FIG. 2c, which are views showing results of reaction activity and selectivity under different temperatures, different catalyst acidities and different DEG/$IB^=$ ratios. As shown in the figures, a first preferred embodiment uses an autoclave. DEG and a cation exchanged resin are put into the autoclave, where the DEG has a 106 grams (g) weight; the resin is Amberlyst 15 having a 11 g weight and a 4.5 meq [$H^+$]/g acidity; and the autoclave has a 600 milliliters (ml) size. Then, a butene mixture is flown in, where the butene mixture has 90% $IB^=$ (about 28 g). Therein, the autoclave is sealed for oil bathing with 2.0 mole ratio of DEG to $IB^=$ ($DEG/IB^=$) and 0.05 more ratio of acidity of the resin to $IB^=$ ($[H^+]/IB^=$), where temperature of the autoclave is controlled between 50 and 110° C. and nitrogen is filled in to obtain a pressure of 200 psi. A reaction is run in the autoclave for 6 hours (hr); and 0.5 ml samples are obtained every a certain minutes for obtaining a conversion rate of $IB^=$ and values of selectivity of DEGtBE, DEGDtBE and octane. As shown in FIG. 2a, a highest $IB^=$ conversion rate is appeared at 60° C.; yet, a higher selectivity of DEGtBE is appeared at 50° C. Hence, a preferred $IB^=$ conversion rate together with a preferred selectivity of DEGtBE is obtained with a reaction temperature between 50 and 60° C.

With the parameters set in FIG. 2a and the same value of DEG/$IB^=$, amounts of the resin used is changed to 6.6 g and 15.4 g; and mole ratios of [$H^+$]/$IB^=$ thus obtained are 0.03 and 0.07. As shown in FIG. 2b, with more resin used, $IB^=$ conversion rate is heightened after 7 hr of reaction under 60° C., where a preferred performance is obtained with a mole ratio of [$H^+$]/$IB^=$ between 0.04 and 0.06.

With the parameters set in FIG. 2a and the same 0.05 mole ratio of [$H^+$]/$IB^=$, a mole ratio of DEG/$IB^=$ is changed to a value between 1.5 and 3.5. As shown in FIG. 2c, with a higher mole ratio of DEG/$IB^=$, $IB^=$ conversion rate and DEGtBE selectivity are heightened after 6 hr of reaction under 60° C., where a preferred performance is obtained with a mole ratio of DEG/$IB^=$ between 2.0 and 3.0.

Please refer to FIG. 3a to FIG. 3c, which are a view showing results of reaction activity and selectivity of the second preferred embodiment under different temperatures, different DEG/$IB^=$ ratios and different WHSVs. As shown the figures, a second preferred embodiment uses a device for a continuous fixed-bed reaction. DEG and a butene mixture are filled in a up-flow way with a liquid chromatography (LC) pump, where the butene mixture has 50% of IB$^=$. A reaction tube of the device is heated through a circular hot water bath, where the tube is 50 centimeters long and has a ½ inches diameter; and the tube is filled with 55.5 g of an acidic cation exchanged resin of Amberlyst 15 as a catalyst. A temperature of a reaction in the tube is controlled between 45 and 80° C.; a mole ratio of DEG/IB$^=$ is 2.0; and a mole ratio of WHSV is 1.20 h$^{-1}$. A sample is taken every hour for obtaining an IB$^=$ conversion rate and a value of product selectivity. As shown in FIG. 3a, a highest IB$^=$ conversion rate is appeared at 55° C.; yet, a highest selectivity of DEGtBE is appeared at 45° C. Hence, a preferred IB$^=$ conversion rate together with a preferred selectivity of DEGtBE is obtained with a reaction temperature between 45 and 55° C.

With the parameters set in FIG. 3a and the same WHSV, a mole ratio of DEG/IB$^=$ is changed to a value between 1.5 and 4.0. As shown in FIG. 3b, with higher mole ratio of DEG/IB$^=$, IB$^=$ conversion rate is heightened, where a preferred IB$^=$ conversion rate and a preferred product selectivity are obtained with a mole ratio of DEG/IB$^=$ between 1.5 and 2.5.

With the parameters set in FIG. 3a and the same value of DEG/IB$^=$, WHSV is changed to a value between 0.6 and 2.4. As shown in FIG. 2c, with a higher WHSV, IB$^=$ conversion rate and DEGtBE selectivity are heightened under 55° C., where a preferred performance is obtained with WHSV between 1.2 and 2.0 h$^{-1}$.

Please refer to FIG. 4, which is a view shown separation and purification. As shown in the figure, the present invention uses two stages of vacuum distillations. The first stage is a low vacuum distillation. Some water is added during azeotrope into a distillate obtained through the distillation to bring out DEGDtBE while an upper layer of DEGDtBE and a lower layer of water are separated owing to the reduction of DEGDtBE in the distillate. Then, the water at the lower layer is recycled to the distillate at bottom again and again for effectively separating the DEGDtBE byproduct. Then, DEG and DEGtBE left on the distillate are separated in the second stage of a high vacuum distillation.

Please refer to FIG. 5, which is a view showing transetherification of DEGDtBE under different temperatures. As shown in the figure, for further confirming a transetherification, DEG is not added with IB$^=$, but rather 10 wt % of DEGDtBE, for reaction under the same conditions as described in FIG. 2a. Reaction temperatures are changed during 6 hr for calculating conversion rates of DEGDtBE and moles of reactant DEGtBE produced per mole of DEGDtBE. As the results show, a higher temperature makes a higher DEGDtBE conversion rate as well as more DEGtBE produced. During the reaction, DEGDtBE may have a transetherification with DEG to produce 2 molecules of DEGtBE; 1 molecule of DEGtBE and 1 molecule of C4; or, 1 molecule of DEG and 2 molecule of C4. If DEGDtBE is added with the reactants of DEG and C4 (ie. recycling the DEGDtBE byproduct to a reactor after a separation in a first stage), cracking reaction can be diminished. Thus, the production of DEGDtBE can be restrained on processing the main transetherification.

Please refer to FIG. 6, which is a view showing cracking reactions of DEGDtBE under different temperatures. As shown in the figure, for further distinguishing transetherification from cracking reaction, DEGDtBE is processed through a cracking reaction with toluene having 10 wt % DEGDtBE. Under the same conditions as described in FIG. 2a, results obtained with temperatures changed during 6 hr show the followings: DEGDtBE conversion rate increases as the temperature increases; no cracking reaction happens below 50° C.; and, only DEGtBE, no DEG, are obtained below 90° C., which shows only 1 molecule of C4 is obtained from DEGDtBE here.

To sum up, the present invention is a method of fabricating DEGtBE using IB$^=$ and DEG, where IB$^=$ and DEG are used with a solid acid catalyst to effectively obtain product of DEGtBE having high selectivity and high purity through two stages of vacuum distillations under certain conditions; and byproduct of DEGDtBE is recycled for reaction while solving amount of IB$^=$ is heightened, transetherification is processed with DEG and the byproduct is restrained from generating.

The preferred embodiments herein disclosed are not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method of fabricating diethylene-glycol tert-butyl ether (DEGtBE) using isobutylene (IB$^=$) and diethylene glycol (DEG), comprising steps of:
    (a) obtaining DEG and IB$^=$ to be mixed in a reactor together with a catalyst of an acidic cation exchanged resin to obtain a glycol ether mixture, wherein said reactor has a reaction temperature between 30 and 150 Celsius degrees (° C.) and a reaction pressure between 15 and 500 pounds per square inch (psi); wherein said catalyst has a mole ratio of acidity to IB$^=$ ([H$^+$]/IB$^=$) between 0.01 and 1.00; and wherein said DEG has a mole ratio to IB$^=$ (DEG/IB$^=$) between 0.5 and 10.0;
    (b) processing said glycol ether mixture through a first stage of vacuum distillation then a second stage of vacuum distillation,
    said first stage being a low vacuum water extraction distillation to separate octane and a byproduct of diethyleneglycol di-tert-butyl ether (DEGDtBE), wherein said first stage has a pressure between 50 and 500 torr and a temperature between 50 and 150° C.; and wherein water added in said first stage has a weight ratio to said glycol ether mixture between 0.1 and 5.0,
    said second stage being a high vacuum distillation to separate un-reacted DEG and a product of DEGtBE, wherein said second stage has a pressure between 0.1 and 10 torr and a temperature between 50 and 150° C.; and
    (c) recycling said byproduct of DEGDtBE separated in said first stage into said reactor to process a transetherification with said DEG, wherein said DEGDtBE has a weight ratio to said DEG between 0.002 and 1.0.

2. The method according to claim 1, wherein said [H$^+$]/IB$^=$ in step (a) lies between 0.04 and 0.06.

3. The method according to claim 1, wherein said DEG/IB$^=$ in step (a) lies between 2.0 and 3.0.

4. The method according to claim 1, wherein said reaction temperature in step (a) lies between 50 and 60° C.

5. The method according to claim 1, wherein said reaction pressure in step (a) lies between 50 and 200 psi.

6. The method according to claim 1, wherein said DEG obtained in step (a) has a content that lies between 10 and 100 weight percents (wt %).

7. The method according to claim 1, wherein said IB$^=$ in step (a) is obtained in a C4 mixture and has a content rate that lies between 10 and 100 wt %.

8. The method according to claim 1, wherein said catalyst in step (a) is a cation exchanged resin having sulfo group (—SO$_3$H) obtained through acidification.

9. The method according to claim 1, wherein said water added in said first stage in step (b) has a weight ratio to said glycol ether mixture between 0.25 and 1.0.

10. The method according to claim 1, wherein said pressure in said first stage in step (b) lies between 100 and 200 torr.

11. The method according to claim 1, wherein said temperature in said first stage in step (b) lies between 65 and 105° C.

12. The method according to claim 1, wherein said pressure in said second stage in step (b) lies between 0.3 and 1.0 torr.

13. The method according to claim 1, wherein said temperature in said second stage in step (b) lies between 80 and 110° C.

14. The method according to claim 1, wherein said weight ratio of DEGDtBE to said DEG lies between 0.01 and 0.1.

15. The method according to claim 1, wherein said DEGDtBE recycled in step (c) contains DEGDtBE and has a weight ratio between 1 and 100 wt %.

16. The method according to claim 1, wherein step (a) uses a device to process a continuous fixed-bed reaction with DEG, $IB^=$ and said catalyst of said acidic cation exchanged resin; wherein said reaction has a temperature between 30 and 150° C. and a pressure between 15 and 500 psi;
wherein said DEG has a mole ratio to $IB^=$ between 0.5 and 10.0; and wherein said reaction has a weight hourly space velocity (WHSV) between 0.1 and 10.0 per hour ($h^{-1}$).

17. The method according to claim 16, wherein said reaction has a temperature between 45 and 55° C.

18. The method according to claim 16, wherein said reaction has a pressure between 50 and 200 psi.

19. The method according to claim 16, wherein said mole ratio of DEG to $IB^=$ lies between 1.5 and 2.5.

20. The method according to claim 16, wherein said WHSV lies between 1.2 and 2.0 $h^{-1}$.

* * * * *